United States Patent [19]

Westenskow et al.

[11] Patent Number: 5,131,401
[45] Date of Patent: Jul. 21, 1992

[54] METHOD AND APPARATUS FOR MONITORING NEUROMUSCULAR BLOCKAGE

[75] Inventors: Dwayne R. Westenskow; Joseph A. Orr, both of Salt Lake City, Utah

[73] Assignee: Axon Medical Inc., Salt Lake City, Utah

[21] Appl. No.: 580,294

[22] Filed: Sep. 10, 1990

[51] Int. Cl.$^5$ ............................................. H61B 15/05
[52] U.S. Cl. ..................................... 128/741; 128/782
[58] Field of Search .................... 128/662.03, 670, 672, 128/675, 680, 686, 687, 689, 690, 691, 714, 721, 722, 733, 741, 774, 782, 82.1; 310/311, 800

[56] References Cited

U.S. PATENT DOCUMENTS

| | | | |
|---|---|---|---|
| 3,903,733 | 9/1975 | Murayama et al. | 73/574 |
| 4,122,837 | 10/1978 | Leonard | 128/774 |
| 4,157,087 | 6/1979 | Miller et al. | 128/741 |
| 4,291,705 | 9/1981 | Severinghaus et al. | 128/733 |
| 4,307,728 | 12/1981 | Walton | 128/687 |
| 4,387,723 | 6/1983 | Atlee et al. | 128/734 |
| 4,595,018 | 6/1986 | Rantala | 128/733 |
| 4,685,469 | 8/1987 | Keller | 128/675 |
| 4,734,044 | 3/1988 | Radice | 439/78 |
| 4,817,628 | 4/1989 | Zealear et al. | 128/741 |
| 4,848,359 | 7/1989 | Bournonville | 128/741 |
| 4,852,581 | 8/1989 | Frank | 128/672 |
| 4,960,128 | 10/1990 | Gordon et al. | 128/677 |
| 4,989,615 | 2/1991 | Hochberg . | |

FOREIGN PATENT DOCUMENTS 230768A 11/1985 German Democratic Rep. .

OTHER PUBLICATIONS

"Self-Tuning, Microprocessor-based Closed-loop Control of Atracurium-induced Neuromuscular Blockade" by P.C. Uys et al., British Journal of Anesthesiology (1988), 61, pp. 685-692.

"New Developments in Clinical Monitoring of Neuromuscular Transmission: Measuring the Mechanical Response" by J. Viby-Mogensen, et al., pp. 56-59.

"Computer-Controlled Muscle Paralysis with Atracurium in the Sheep" by D. G. Lampard et al., Anesthesia and Intensive Care, vol. 41, (1986) pp. 316-320.

"Closed-loop Adminstration of Atracurium", by N. R. Webster et al., Anesthesia vol. 42 (1987) pp. 1085-1091.

"Measuring the compound EMG in the Use of Muscle Relaxants" by J. F. Crul et al., Escerpta Medica (1983) pp. 60-65.

"A Comparison of Computer-Controlled Versus Manual Administration of Vecuronium in Humans" by R. R. Jaklitsch et al., Journal of Clinical Monitoring, vol. 3, No. 4 (1987) pp. 269-276.

"Clinical automatic control of neuromuscular blockage," by A. J. Asbury, et al., Anesthesia vol. 41 (1986) pp. 316-320.

"Clinical Assessment of Neuromuscular Transmission" by J. Viby-Mogenson, British Journal of Anesthesiology, vol. 54 (1982) pp. 209-223.

Primary Examiner—Stephen C. Pellegrino
Assistant Examiner—Steven J. Shumaker
Attorney, Agent, or Firm—Trask, Britt & Rossa

[57] ABSTRACT

The present invention comprises a method and apparatus for monitoring neuromuscular blockage, and more specifically contemplates the quantitative measurement of movement of the skin of a patient overlying an electrically simulated skeletal muscle as an indicia of such blockage. The preferred embodiment of the apparatus of the present invention includes a piezoelectric film affixed over the patient's skin, the film generating an electric current in proportion to the magnitude of skin movement.

17 Claims, 4 Drawing Sheets

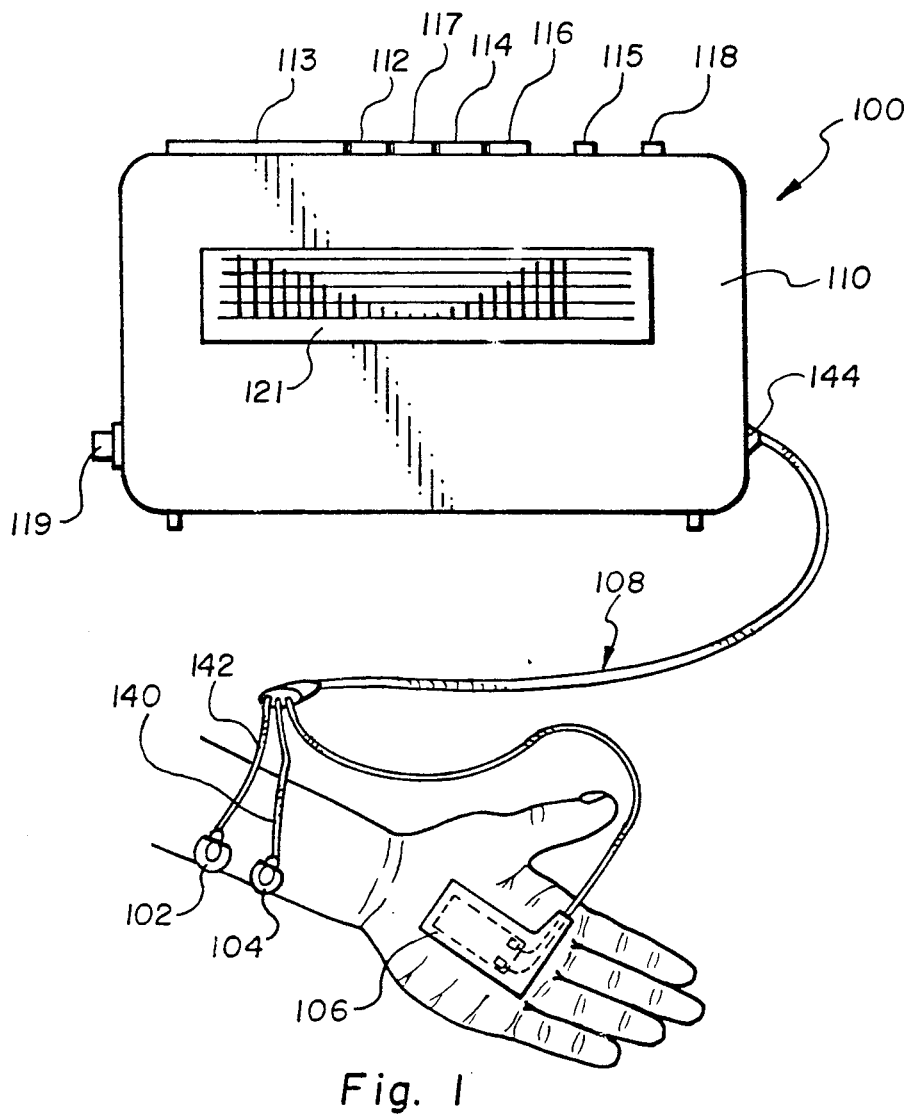
Fig. 1
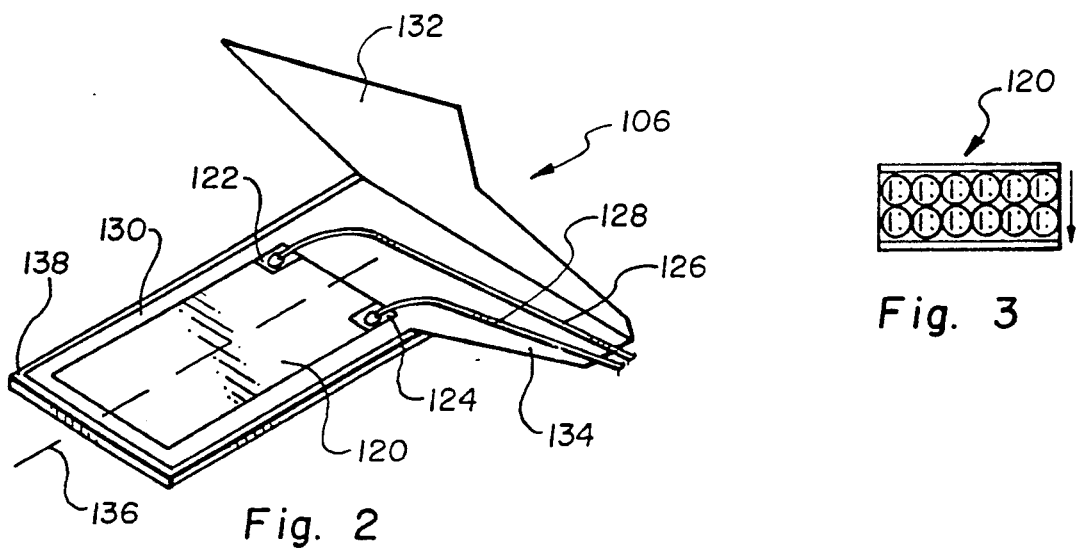
Fig. 2
Fig. 3

METHOD AND APPARATUS FOR MONITORING NEUROMUSCULAR BLOCKAGE

BACKGROUND OF THE INVENTION

The present invention relates generally to the monitoring of neuromuscular function in humans, and more specifically to an apparatus and method for monitoring neuromuscular blockage during induction of anesthesia prior to an operation, during the operation itself, during the reversal of the neuromuscular block and after the operation is complete.

During the past four decades, muscle relaxants have been used routinely during anesthesia to facilitate endotracheal intubation, to simplify the control of artificial respiration, and to make intra-abdominal and thoracic operations possible. More recently, the use of muscle relaxants in intensive care units has gained widespread acceptance for intubation, to permit decreased ventilator pressures and to reduce patient oxygen consumption.

A significant drawback to the use of neuromuscular blocking agents is the wide variation and lack of predictability of patient response thereto. Even in healthy patients, there are large individual differences in sensitivity, which may be aggravated by disease (myasthenia gravis), hypothermia, disturbed acid-base balance and altered liver and kidney function. Suffice it to say, patient response is unpredictable to the extent that clinical evaluation thereof has proved to be inadequate in a large number of instances.

The most serious side effect of an overdose of muscle relaxant is post operative respiratory failure, generally termed residual curarization by the medical community. After anesthesia has ended, the patient may not be able to breathe because of weak respiratory muscle strength. This hazard alone has called for a means to effectively assess neuromuscular blockage to that muscle relaxant overdose can be avoided, as the assumption that relaxation has been reversed and that a patient is capable of self-sustaining respiration can only be ascertained when neuromuscular function is accurately measured.

Muscle relaxation is commonly measured during induction of anesthesia, during the operation, during the reversal of the neuromuscular block and after completion of the operation. Generally, aside from clinical observation by the anesthesiologist of unstimulated muscle movement, a technique which is highly subjective and virtually impossible with unconscious patients, electrical nerve stimulation is currently the preferred monitoring technique. One prior art apparatus for providing such stimulation is disclosed in U.S. Pat. No. 4,157,087.

A nerve stimulator is attached to a motor nerve of the patient before induction of anesthesia, and is switched on after the patient is asleep. An electrical stimulation current is then applied to the nerve, and those muscles supplied by the nerve will contract. There is maximum contraction of a muscle fiber if stimulus intensity exceeds a certain threshold. The incremental increase in the force of muscle contraction is graded by and proportional to the number of muscle fibers activated. If the motor nerve is stimulated sufficiently, as by a current of adequate magnitude, all of the muscle fibers supplied by the nerve will contract and the maximum force of contraction is obtained. Further increase in stimulus intensity, or application of a supramaximal stimulus, does not increase contraction force. It is desirable to increase the electrical stimulus gradually until the supramaximal level is reached, to provide a baseline response. However, many practitioners do not utilize supramaximal stimuli due to the attendant acute patient discomfort. It is also possible for the practitioner to utilize a lesser level of electrical stimulation, and to follow the trend of neuromuscular blockage as anesthesia is induced.

Once the maximum muscle reaction is known to a reference stimulation, a myoneural blocking drug is injected. In most situations, a drug dose which produces a depression of 90-95% of muscle response, generally termed 90-95% "twitch" depression, is adequate to ensure sufficient muscle relaxation while facilitating antagonism of the postoperative block.

Various techniques have been employed in the prior art to monitor patients' muscular reactions to electrical nerve stimuli. The first, visual or tactile observation of muscle movement following electrical stimulation, has been shown to be inadequate in identifying fade is muscle response with sufficient accuracy to exclude residual curarization.

The second, use of a force transducer to measure strength of muscle response to stimulation of the ulnar nerve, requires that the patient's hand and thumb be restrained and connected to a force transducer and monitor. Such devices are disclosed in U.S. Pat. No. 4,387,723 and 4,848,359, and in "Self-Tuning, Microprocessor-based Closed-loop Control of Atracurium-induced Neuromuscular Blockade" by P. C. Uys et al, *British Journal of Anesthesiology* (1988), 61, pp. 685-692 and "New Developments in Clinical Monitoring of Neuromuscular Transmission: Measuring the Mechanical Response" by J. Viby-Mogensen et al, pp. 56-59. Aside from being both cumbersome and costly to implement, the method may result in nerve or tissue damage if the thumb is not positioned properly with respect to the transducer linkage, due to the necessarily rigid connection thereto.

A third technique, evoked electromyography, or EMG, records the compound action potential caused by stimulation of a peripheral nerve. EMG devices and methods are disclosed in U.S. Pat. No. 4,291,705 and 4,595,018, and in "Computer-Controlled Muscle Paralysis with Atracurium in the Sheep" by D. G. Lampard et al, *Anaesthesia and Intensive Care*, Vol. 14, No. 1, (1986) pp. 7-11; "Clinical automatic control of neuromuscular blockade", by A. J. Asbury et al, *Anesthesia*, Vol. 41 (1986) pp. 316-320; "Closed-loop administration of atracurium" by N. R. Webster et al, *Anesthesia* Vol. 42 (1987) pp. 1085-1091; and "Measuring the compound EMG in the use of muscle relaxants" by J. F. Crul et al, *Excerpta Medica* (1983) pp. 60-65. EMG signal amplitude is typically in the range of 3 uV to 5,000 uV, the duration about 3 ms to 15 ms, and the frequency range 2 Hz to 10,000 Hz. While surface electrodes are conveniently employed to noninvasively record the overall electrical activity of the muscles, good electrical contact is difficult to maintain at the skin/electrode interface, and the system, due to the small magnitude and short duration of the signals, is difficult to isolate from electrical interference.

Yet another technique of the prior art employ a thumb-mounted miniature accelerometer to measure patient response to stimulation. The method is convenient, but the device is both expensive and fragile and measures movement in only one direction. Thus, accelerometer mounting orientation is critical, as the use of a triaxial accelerometer with attendant hardware and software to resolve the signals would be prohibitively expensive. U.S. Pat. No. 4,817,628 suggests the use of facial-mounted accelerometers, and acknowledges that the use of bi-or triaxial accelerometers may be necessary for meaningful data.

Finally, combinations of several of the above prior art methods and devices have been utilized, as disclosed in "A Comparison of Computer-controlled Versus Manual Administration of Vecuronium in Humans" by R. R. Jaklitsch et al, *Journal of Clinical Monitoring*, Vol. 3, No. 4 (1987) pp. 269–276, wherein both a thumb-mounted force transducer and EMG monitoring are employed.

SUMMARY OF THE INVENTION

In contrast to the prior art, the present invention comprises a reliable and accurate method and apparatus for measuring neuromuscular blockage utilizing a disposable, adhesively affixed transducer which does not require rigid restraint of the part of the patient's body to which the transducer is secured.

More specifically, the present invention employs a disposable piezoelectric sensor in the form of a film adhesively applied to the patient to measure the evoked response (movement) of a skeletal muscle enervated by electrical stimulation of a peripheral nerve. In the preferred embodiment, a monitor unit will automatically administer the electrical stimuli under computer control, and after measuring the resultant movement via the sensor, will graphically display the responses to stimulation over time to indicate the blockage trend.

In contrast to the prior art techniques, piezoelectric sensing of evoked responses does not require patient cooperation, the rigid restraint of a patient extremity, or an expensive sensor requiring precise orientation and/or rigid attachment to the patient. Furthermore, the piezoelectric signal utilized in the present invention is self-generated by the sensor in response to muscle movement, and is thus not subject to interference as are EMG's utilizing a separate power source. Finally, the muscle movements sensed by the present invention may be characterized as micro-movements of underlying muscle sensed by the affixed sensor directly through the skin of the patient rather than the macro-movements of the body extremities and other body portions sensed by the accelerometers and force transducers of the prior art. It is for this reason that restraint of the extremity is not required, as movement of the entire extremity or other body portion will not result in a signal, while "twitch" of the enervated muscle or muscle group on that extremity, will.

BRIEF DESCRIPTION OF THE DRAWINGS

The present invention will be more fully understood by one of ordinary skill in the art through a review of the following detailed description of the preferred embodiments in conjunction with the accompanying drawings, wherein:

FIG. 1 comprises a perspective view of a patient's hand and lower arm having stimulation electrodes and monitoring sensor attached thereto with leadwires to a portable microprocessor based stimulator/monitor control unit, all according to the present invention.

FIG. 2 comprises a perspective view of the preferred embodiment of the sensor of the present invention with its encapsulating film opened.

FIG. 3 comprises a schematic of a poled polymer such as is employed in the piezoelectric film of the sensor of the present invention.

DETAILED DESCRIPTION OF THE PREFERRED EMBODIMENTS

Figure 4:
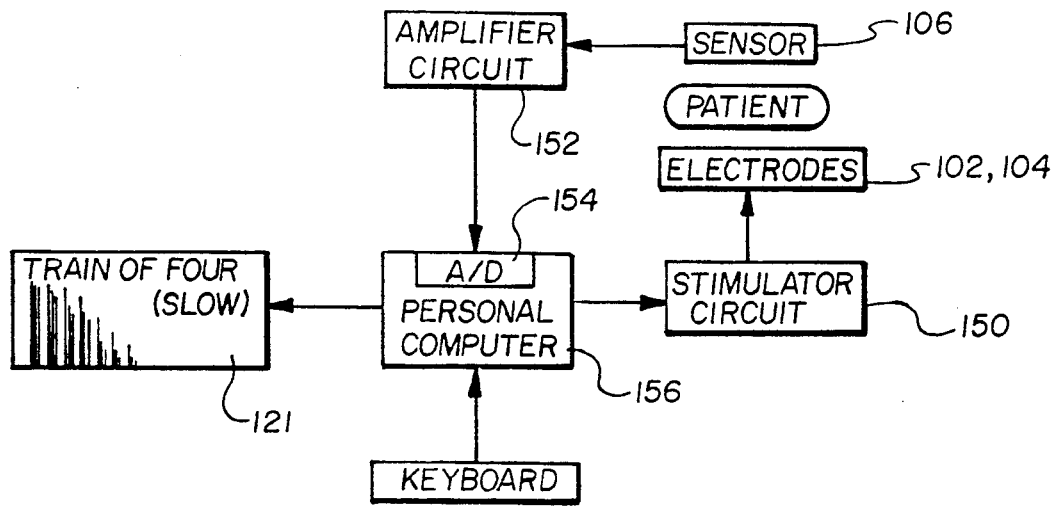
FIG. 4 comprises a schematic of the neuromuscular blockade monitoring system of the present invention.

Referring now to FIG. 1 of the drawings, the apparatus of the present invention for measuring neuromuscular blockage, also referred to hereinafter as a twitch monitor, will be generally described.

Twitch monitor 100 includes stimulation electrodes 102 and 104 and motion sensor 106 all linked via wiring harness 108 to battery powered stimulator/monitor control unit 110. The electrodes may be any commercially available electrodes, such as silver/silver chloride stimulation electrodes available from the NDM Division of Baxter corporation, while sensor 106 is unique and comprises part of the present invention. Various control buttons 112-118 are mounted on the exterior of unit 110 for instituting electrical stimuli of varying type and frequency to the patient via electrodes 102 and 104, gain control knob 119 is utilized by the practitioner to control the magnitude of the electrical stimuli, and response display screen 121, preferably of the back-lit LCD type, is mounted on the front of control unit 110 and displays responses to stimuli. The foregoing items will be described in greater detail later in connection with the operation of the apparatus of the present invention according to the method thereof.

Referring to FIG. 2, motion sensor 106 preferably comprises a piezoelectric polymer film 120 which creates an electrical current in response to movement of any part of the polymer. By way of background, piezoelectricity can be described as "electric polarization produced by mechanical strain in crystals, the polarization being proportional to the amount of strain and changing sign with it", W. G. Cady, *Piezoelectricity*. Although the piezo film polymer 120 employed in the present invention is not crystalline in structure, it responds according to the same principle. One preferred polymer, polyvinylidene fluoride (PVDF), is a long chain semi-crystalline polymer of the repeat unit ($CH_2$—$CF_2$) which is "poled" during the beta phase of the polymer by exposing the polymer to an oriented electrical field at elevated temperatures. Correct poling creates permanent orientation of molecular dipoles in the polymer as shown in FIG. 3, the resulting structure yielding alignment and activity similar to that of a piezoelectric crystal. The piezo film as described above being known in the prior art and commercially available as a Kynar piezo film from Penwalt, Inc. of Valley Forge, Pa., further details thereof will not be described as not forming part of the present invention.

In sensor 106 of the present invention, film 120 comprises a 40×15 millimeter strip of 28 micrometer thickness and having pads 122 and 124 at one end thereof for electrical contact with lead wires 126 and 128, respectively, wires 126 and 128 being preferably secured to pads 122 and 124 via beads of electrically conductive epoxy, preferably silver epoxy, such as EPO-TEK 410E silver epoxy from Epoxy Tech, Inc. of Billerica, Mass. Film 120 is encapsulated between two layers of vinyl 130 and 132 having an adhesive coating on one side thereof to secure film 120 and protect it from fluids while having sufficient pliability to permit free movement of film 120 is response to muscle twitches. Lead wires 126 and 128 are preferably routed out the side of the film "sandwich" through a leg 134 created by extensions of vinyl layers 130 and 132 to remove the wires from the primary bending axis 136 of sensor 106, and to mechanically connect and support the lead wires to the sensor independently of the epoxy beads. The sandwiched piezo film is then adhered to one side of a one-sixteenth inch thick polyethylene foam pad 138 having acrylic skin adhesive on the other side thereof for adhesively securing the sensor to the patient. As shown in FIG. 1, the preferred mode of attachment is to the palm of the patient's hand, with an orientation of primary bending axis 136 across the palm creases being preferred for maximum sensor response, the magnitude of the sensor signal generated by the piezo film 120 being directly proportional to the degree of muscle movement evoked in response to stimulation of the associated nerves. Lead wires 126 and 128, which along with electrode lead wires 140 and 142 are bundled in wiring harness 108, end at a common electrical connector 144, which may comprise a commercially available modular telephone jack.

Figure 10:
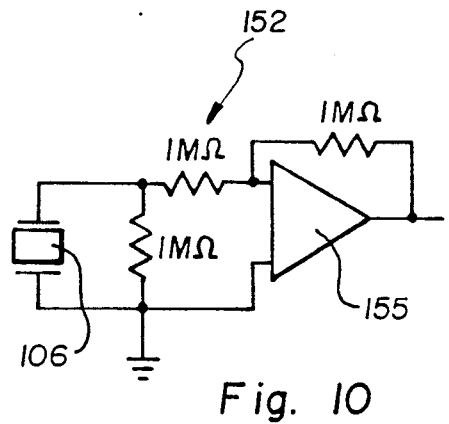
FIG. 10 comprises a schematic of a preferred signal amplifier for use with the present invention.

FIG. 4 of the drawings schematically depicts the major components of twitch monitor 100, including stimulation electrodes 102 and 104, sensor 106 and control unit 110. Control unit 110 includes control buttons 112-118, control knob 119 and LCD display 121, as well as stimulator circuit 150 for providing an electrical pulse through electrodes 102 and 104, and an amplifier circuit 152, which receives and amplifies the signal from sensor 106, which in turn is converted from analog to digital format in A/D converter 154 for processing by microprocessor 156 and display on screen 121. Stimulator circuit 150 may comprise a commercially available device such as the NeuroTechnology, Inc. "Digistim II"; preferred amplifier circuit 152 may be a single operational amplifier circuit as schematically shown in FIG. 10 of the drawings, utilizing a National Semiconductor LM 324 quad operational amplifier chip 155; the A/D converter 154 may be the commercially available Data Translations DT2814, and but it is preferred that the A/D converter 154 be included with microprocessor 156, which is preferably an Hitachi H8/532 single chip microcomputer available from Hitachi America Ltd., San Jose, Calif. The H8/532 includes not only an A/D converter, but digital input-output lines and program and storage memory. The digital output lines are used to drive the stimulator circuit 150 and the display 121, while the digital input lines are used to receive user commands via control buttons 112-118.

The twitch monitor 100 is software controlled in response to the input from control buttons 112-118 to deliver several stimulation modes, with the stimulation pulse current being user variable via gain control knob 119 between 30 to 100 mAmp at 1 msec duration, according to the level of stimulation desired.

Control button 112 elicits a single twitch mode of stimulation, applied at a frequency of one (1) Hz. Muscle response due to single twitch stimulation depends upon both frequency and duration of stimulation. A control reading for supramaximal or lesser stimulation, at the discretion of the practitioner, is applied prior to paralysis of the patient, and subsequent evoked single twitches are measured as a fraction of control response. For low levels of paralysis, single twitch stimulation is not as sensitive as train-of-four stimulation, discussed below, but intense neuromuscular blockade is still detectable via single twitch stimulation.

Control button 113 elicits supramaximal tetanic stimulation at a frequency of 50 Hz and a duration of 5 s. Such stimulation is not preferred, as tetanic stimulation itself alters neuromuscular transmission, the phenomenon of interest, as the response decreases in strength during the period of stimulation; this is referred to as "tetanic fade". Tetanic fade is itself employed to assess the adequacy of recovery from nondepolarizing neuromuscular block. Tetanic stimulation may also be useful due to the phenomenon of post-tetanic potentiation in which the response (twitch) evoked after tetanic stimulation is higher than the twitch evoked prior to tetanic stimulation, particularly when response to single or train-of-four (TOF) stimulation is absent.

Control button 113 results in train-of-four (TOF) stimulation applied at the rate of 2 Hz. In TOF stimulation, four single stimulate and measure sequences are executed at equal intervals; in the present invention, the intervals are preferably of 500 msec.

Control button 114 commands an automated sequence of single twitch stimuli at the rate of 1/sec or 1/30 sec, depending upon the position (slow or fast) of button 115. Similarly, button 116 commands an automated sequence of TOF stimuli executed at 500 msec stimulation pulse intervals at train intervals of one TOF every 10 sec or one TOF every minute, again depending upon the position of button 115. Finally, button 117 institutes a calibration cycle comprising a single stimulate and measure cycle, executed prior to administration of muscle relaxants. The resulting sensor measurement corresponds to 100% movement of the stimulated muscle responsive to the maximum applied electrical stimulation. Button 118 turns on the control unit 110 and the backlighting for screen 121 on and off.

Figure 5:
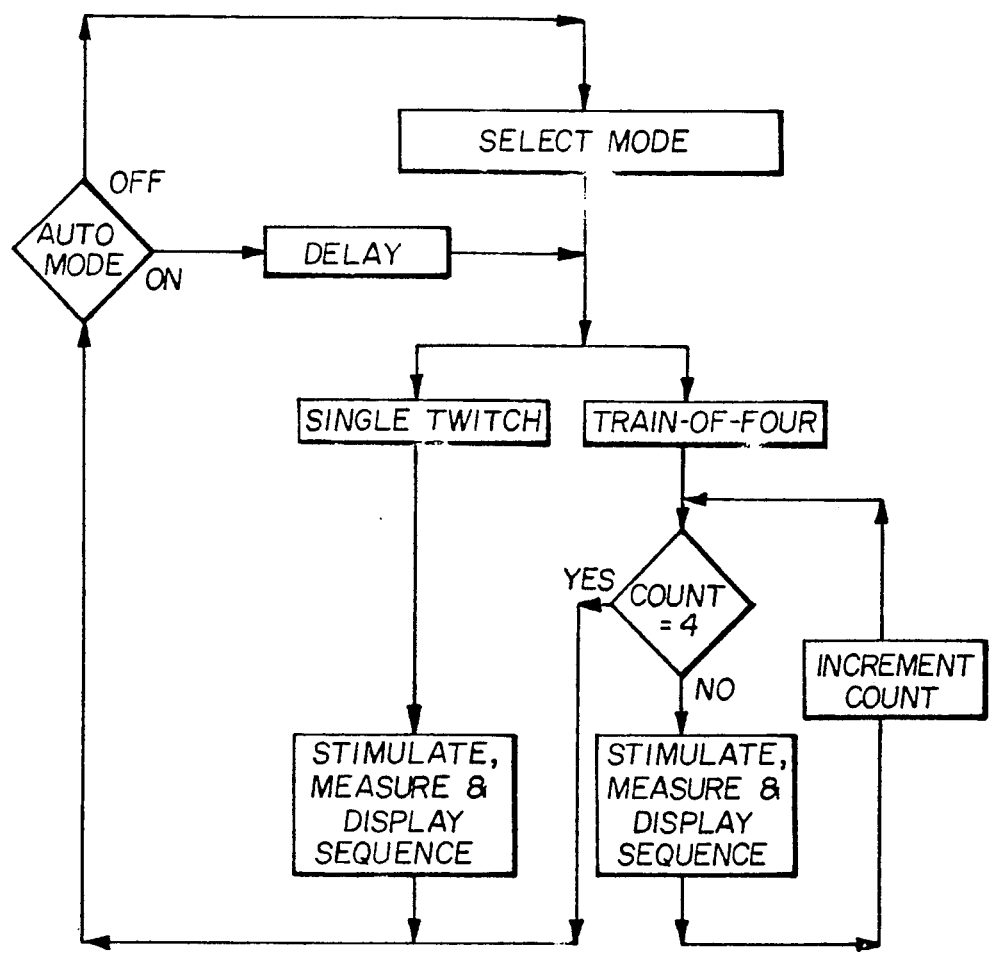
FIG. 5 comprises a system flowchart for operation of the system of FIG. 4.

Reference to FIG. 5 will graphically illustrate the variety of stimuli deliverable with unit 110 to electrodes 102 and 104 in the operation of twitch monitor 100.

Figure 6:
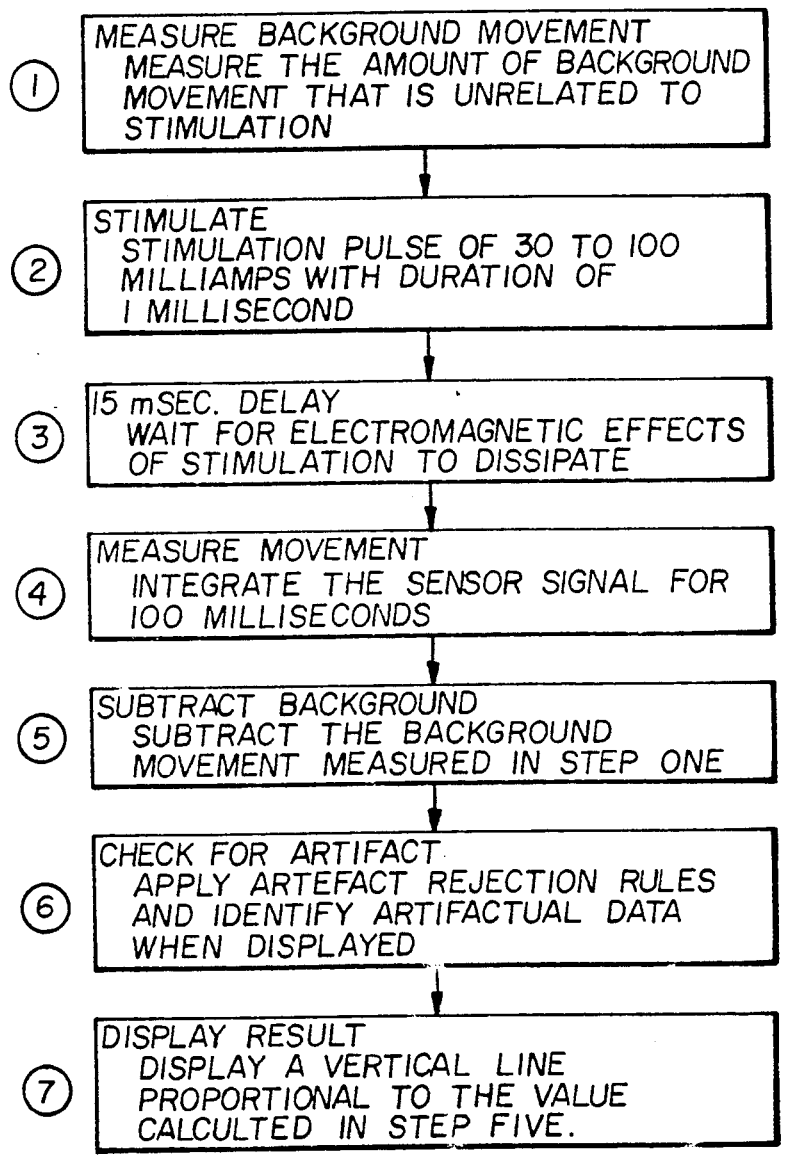
FIG. 6 comprises a flow diagram of the method of the present invention.

The flow diagram of FIG. 6 reflects the routines of the computer program controlling the system. Step 1, sampling of background movement, measures and records any signals unrelated to electrical muscle stimulation as a baseline immediately prior to a stimulation and measurement sequence, so that the amount of signal corresponding to stimulation can be accurately recorded. Step 2, muscle stimulation, results in pulse application to the skin directly over the nerve controlling the muscle over which the sensor 106 is applied. Step 3, a 15 msec delay, provides for dissipation of an electrical charge capacitively stored in sensor 106 as a result of the stimulation pulse of Step 2 prior to measurement of muscle movement. Movement is measured in Step 4 by sensor 106, the signal is rectified and integrated by summation of digitized samples taken at a rate of 500 per sec for a period of 100 msec following the 15 msec delay. In Step 5, background measurement from Step 1 is subtracted from the measured value in Step 4. In step 6, artifact rejection rules hereinafter set forth are applied to identify and reject background noise. Finally, in Step 7 a vertical line is drawn on display screen 126 as a graphical display of muscle response as a percent of the control, or calibration, response.

To successfully apply electrical stimulation for monitoring purposes, an effective methodology of artifact rejection must be employed. The term "artifact" includes noise in the measurements caused by electrocautery and surgeon induced patient movement. Artifactual readings can be identified using simple rules relating each measurement to prior ones as follows:

Rule 1: $T_1 > T_2 > T_3 > T_4$

Rule 2: $T_i < 100\%$

Rule 3: $T_1(t) < 3 \times T_1(t-1)$

Rule 4 $|T_4 \text{ ratio}(t) - T_4 \text{ ratio }(t-1)| < 30\%$

According to Rule 1, each of the four evoked twitches in a TOF responses ($T_1, T_2, T_3, T_4$) must be less than the previous one in the same TOF; if this is not the case, the reading is discarded. According to Rule 2, the four individual twitches ($T_i$) in a TOF sequence must each be weaker than the control response, so twitches which exceed the supramaximal response are assumed to be contaminated by noise and rejected. Pursuant to Rule 3, single twitch responses which are more than three times larger than the prior single twitch response are disregarded as, even during reversal of neuromuscular blockade, an increase in twitch strength of 300% within 20 seconds is impossible. Finally, Rule 4 provides that a change in TOF ratio of more than 30% in 20 seconds indicates artifact. In addition to the four rules, it has also been established by the inventors that, for non-depolarizing neuromuscular blocking agents, the fourth evoked twitch in a TOF is always weaker than the first, or TOF ratio < 100%, so signals defying this observation are rejected.

After artifact rejection, the final step in the measurement process is comparison of the integrated signal to a reference value, which is acquired as noted above prior to the induction of anesthesia and represents the amount of skin movement resulting from the applied control stimulation prior to administration of neuromuscular blocking agents. All subsequent measurements are then presented as a percentage of the reference value, referencing thus making the monitor independent of sensor position and level of stimulation as long as these remain constant during monitoring.

For safety, the system measures the stimulation current each time the stimulator circuit 150 is activated. The absence of any current in either or both of the stimulator leads 140 and 142 indicates disconnection or lack of electrical contact with the skin of the patient and is indicated to the user. If the stimulator current is changed by the user and a new reference value has not been recorded, the values recorded after the change are considered invalid and the user is advised via the display screen.

In addition to the active safety features of the twitch monitor of the present invention, the invention inherently errs toward safety in the event of a system failure. For example, if the sensor 106 is removed or partially disconnected, the resulting diminished sensed skin movement measurement would indicate the presence of significant muscle relaxation, with a user response of reduced or terminated administration of blocking agents. A similar result follows for loss of stimulation or low battery levels.

Figure 7A:
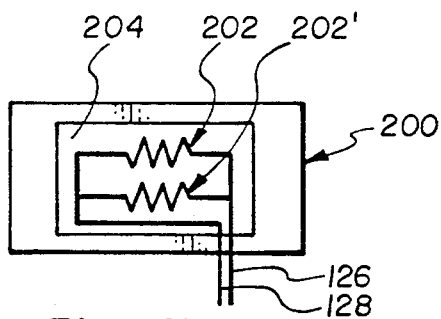
FIG. 7A is a top elevation taken along line A—A of FIG. 7.
Figure 7:
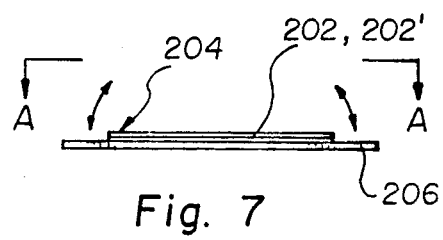
FIG. 7 comprises a first preferred alternative embodiment of the sensor of the present invention.

FIG. 7 graphically depicts an alternative embodiment 200 of the sensor of the present invention. Sensor 200 may employ one or more resistance type strain gauges 202 and 202' encapsulated in a vinyl sheath 204 adhesively securable to the patient's skin via adhesive coated foam pad 206. The strain gauges may be of the carbon film or other suitable commercially available type. As the patient's skin moves during a twitch, the resistance of the strain gauge to the passage of an electrical current therethrough via lead wires 126 and 128 will vary in proportion to the movement and which, as in the preferred embodiment, is compared to a control response.

Figure 8:
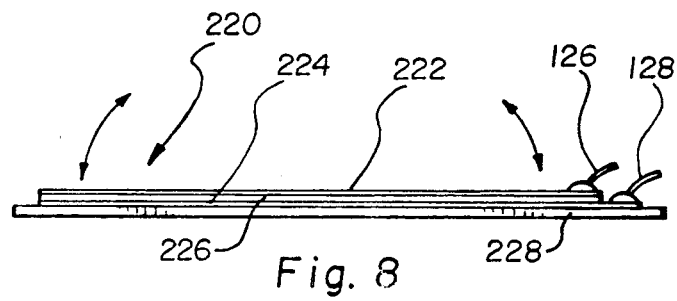
FIG. 8 comprises a second preferred alternative embodiment of the sensor of the present invention.

FIG. 8 depicts a second alternative embodiment 220 of the sensor of the present invention using two substantially parallel thin metal plates or leaves 222 and 224 having a dielectric substrate 226 disposed therebetween, the assembly again being attached to the skin of the patient by an adhesive coated foam pad 228. Sensor 220 thus comprises a capacitor, the capacitance thereof and therefore the voltage response varying with muscle movement (twitches), the signal being picked off via lead wires 126 and 128.

Figure 9:
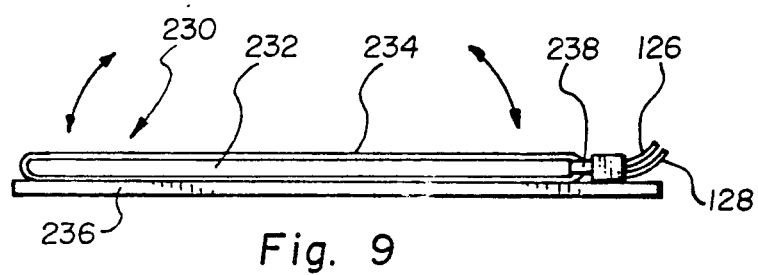
FIG. 9 comprises a third preferred alternative embodiment of the sensor of the present invention.

FIG. 9 depicts a third alternative embodiment 230 of the sensor of the present invention using an open-cell foam pad 232 encapsulated in a rubber bladder. 234, the assembly again adhesively attached to the patient by foam pad 236. Patient twitches will result in compression of the foam and thus the available volume for gas, such as nitrogen, within the bladder 234, raising the pressure and density thereof, the magnitude of which can be measured and converted to an electrical signal as known in the art, for example by the change in resonant frequency of a small quartz resonator within the bladder, or by capacitance or strain-type pressure sensors. A sensor of suitable design is generally designated in FIG. 9 by reference numeral 238.

It will be apparent to the skilled practitioner in the art that a novel and unobvious, simple and reliable method and apparatus for monitoring neuromuscular blockade has been invented. As noted previously, the use of sensors sensitive only to the muscle twitch phenomenon itself via direct attachment to the skin of the patient eliminates many opportunities for measurement error due to patient movement and electrical interference, as well as potential for patient injury.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. For example, any programmable microcomputer may be employed to control the system; other types of displays may be employed; audio alarms may be added to alert the practitioner to unacceptably high levels of blockade, the sensor may be incorporated in a glove for application to the patient's hand, may be affixed to the patient with velcro tabs or strips, or may be applied to a suitable portion of the face or other part of the patient's body, etc., in any of the above-referenced manners.

We claim:

1. An apparatus for monitoring neuromuscular blockage in a patient, comprising:
   means for providing electrical stimulation to a peripheral nerve of said patient; and means for measuring the degree of response evoked in a skeletal muscle of said patient by said electrical stimulation of said peripheral nerve, said measuring means including:
- a flexible film of piezoelectric material for generating an electrical signal generally proportional to the degree of deflection thereof;
- nonconductive material substantially encapsulating said piezoelectric film;
- thin, flexible pad means for supporting said substantially encapsulated piezoelectric film, said pad means having one side secured to said piezoelectric film and another side for application to the skin of the patient; and
- means for securing said thin, flexible pad means over the skin of said patient in overlying relationship to said skeletal muscle.

2. The apparatus of claim 1, wherein said means for securing comprises an adhesive.

3. The apparatus of claim 2, wherein said adhesive is disposed over substantially the entire said another side of said pad means.

4. The apparatus of claim 1, wherein said measuring means further includes first and second lead wires conductively attached to said piezoelectric film.

5. The apparatus of claim 4, wherein said piezoelectric film includes a primary bending axis, and said first and second lead wires are attached to said film at locations removed therefrom.

6. The apparatus of claim 4, further including contact pads on said piezoelectric film, by which said first and second lead wires are conductively attached thereto.

7. The apparatus of claim 4, wherein said electrically nonconductive material defines a leg extending peripherally beyond said piezoelectric film, and said lead wires extend from said piezoelectric film through said leg and beyond said nonconductive material.

8. An apparatus for monitoring neuromuscular blockage in a patient, comprising:
   means for providing electrical stimulation to a peripheral nerve of said patient; and
   means for measuring the degree of response evoked in a skeletal muscle of said patient by said electrical stimulation of said peripheral nerve, said measuring means including:
   an electrical power source;
   flexible strain gauge means in communication with said electrical power source for varying the electrical resistance to power from said power source in response to the degree of deflection of said flexible strain gauge means;
   nonconductive material encapsulating said flexible strain gauge means;
   thin, flexible pad means for supporting said flexible strain gauge means, said pad means having one side secured to said strain gauge means and another side for application to the skin of the patient; and
   means for securing said thin, flexible pad means over the skin of said patient in overlying relationship to said skeletal muscle.

9. The apparatus of claim 8, wherein said means for securing comprises adhesive.

10. An apparatus for monitoring neuromuscular blockage in a patient, comprising:
    means for providing electrical stimulation to a peripheral nerve of said patient; and
    means for measuring the degree of response evoked in a skeletal muscle of said patient by said electrical stimulation of said peripheral nerve, said measuring means including:
    a flexible, variable capacitor comprising two flexible, substantially parallel, thin conductive members having a flexible dielectric substrate disposed therein;
    first and second electrical conductors each communicating with one of said members and extending to an electrical power source;
    thin, flexible pad means for supporting said flexible, variable capacitor, said pad means having one side secured to said variable capacitor and another side for application to the skin of the patient; and
    means for securing said thin, flexible pad means over the skin of said patient in overlying relationship to said skeletal muscle.

11. The apparatus of claim 10, wherein said means for securing comprises adhesive.

12. An apparatus for monitoring neuromuscular blockage in a patient, comprising:
    means for providing electrical simulation to a peripheral nerve of said patient; and
    means for measuring the degree of response evoked in a skeletal muscle of said patient by said electrical stimulation of said peripheral nerve, said measuring means including:
    a substantially planar, internally resiliently supported, flexible bladder containing a substantially compressible fluid therein,
    means in communication with said fluid for sensing pressure or density changes therein and generating a signal generally proportional to the magnitude of said changes;
    thin, flexible pad means for supporting said flexible, bladder, said pad means having one side secured to said flexible bladder and another side for application to the skin of the patient; and
    means for securing said thin, flexible pad means over the skin of said patient in overlying relationship to said skeletal muscle.

13. The apparatus of claim 12, wherein said means for securing comprises adhesive.

14. A method of measuring neuromuscular blockage in a patient, comprising:
    securing a skin movement sensor in direct contact with the skin of said patient overlying a skeletal muscle;
    measuring background movement of said skin with said skin movement sensor and quantifying said background movement as an electrical parameter;
    electrically stimulating a peripheral nerve of said patient associated with said skeletal muscle to evoke a response therefrom;
    measuring movement of said skin subsequent to said electrical nerve stimulation and during said evoked muscle response with said skin movement sensor, and quantifying said skin movement during said evoked skeletal muscle response as an electrical parameter; and
    subtracting said quantified background movement of said skin from said quantified skin movement measured during said evoked skeletal muscle response.

15. The method of claim 14, further including the step of waiting for electromagnetic effects resulting from said electrical stimulation to dissipate from said skin movement sensor before said step of measuring said skin movement during said evoked skeletal muscle response.

16. The method of claim 14, further including graphically representing the magnitude of said quantified skin movement during said evoked skeletal muscle response after subtraction of said quantified background skin movement therefrom.

17. The method of claim 16, further including the step of identifying artifact in said quantified skin movement during said evoked skeletal muscle response after subtraction of said background skin movement therefrom and removing said artifact therefrom prior to said step of graphically representing.

* * * * *